US010071385B2

(12) United States Patent
Yano et al.

(10) Patent No.: US 10,071,385 B2
(45) Date of Patent: Sep. 11, 2018

(54) CENTRIFUGING SYSTEM, SAMPLE PREPROCESSING SYSTEM, AND CONTROL METHOD

(71) Applicant: HITACHI HIGH-TECHNOLOGIES CORPORATION, Tokyo (JP)

(72) Inventors: Shigeru Yano, Tokyo (JP); Osamu Watabe, Tokyo (JP); Kenichi Takahashi, Tokyo (JP); Takahiro Sasaki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 459 days.

(21) Appl. No.: 14/763,187

(22) PCT Filed: Jan. 17, 2014

(86) PCT No.: PCT/JP2014/050728
§ 371 (c)(1),
(2) Date: Jul. 24, 2015

(87) PCT Pub. No.: WO2014/119378
PCT Pub. Date: Aug. 7, 2014

(65) Prior Publication Data
US 2015/0360239 A1    Dec. 17, 2015

(30) Foreign Application Priority Data
Jan. 30, 2013 (JP) .................. 2013-014962

(51) Int. Cl.
*B04B 5/10* (2006.01)
*B04B 13/00* (2006.01)
(Continued)

(52) U.S. Cl.
CPC .................. *B04B 5/00* (2013.01); *B04B 5/10* (2013.01); *B04B 13/00* (2013.01);
(Continued)

(58) Field of Classification Search
CPC ......... B04B 5/10; B04B 13/00; B04B 5/0407; B04B 9/00; B04B 5/0421; B04B 5/0414;
(Continued)

(56) References Cited

U.S. PATENT DOCUMENTS 3,151,073 A * 9/1964 Anthon .................... B04B 5/04
198/803.9
3,644,095 A * 2/1972 Netheler ............ G01N 35/0092
141/130
(Continued)

FOREIGN PATENT DOCUMENTS

JP    07-234177 A    9/1995
JP    10-216563 A    8/1998
(Continued)

OTHER PUBLICATIONS

International Search Report of PCT JP2014/050728, dated Apr. 2014.

*Primary Examiner* — Charles Cooley
(74) *Attorney, Agent, or Firm* — Mattingly & Malur, PC

(57) ABSTRACT

A sample preprocessing system is capable of reducing centrifuging time, which accounts for the majority of time required for a preprocessing step, and at the same time, performing centrifuging under various conditions. A system management unit ascertains the states of a plurality of centrifuge devices, particularly comparing centrifuging start times and centrifuging termination times for the respective centrifuge devices, and selects the centrifuge device for which the processing time is shortest. Specifically, the system includes an adapter that forms a plurality of batches, a gripper to transfer a sample to the adapter, a plurality of centrifuge rotors that centrifuge the adapter in batch units, and a computer programmed to calculate, in advance, a start timing and a termination timing of the centrifuging in batch units, and the batch, into which samples are transferred, is
(Continued)

controlled on the basis of at least one of the calculated start timing and termination timing.

12 Claims, 8 Drawing Sheets

(51) Int. Cl.
  *B04B 5/00* (2006.01)
  *G01N 35/00* (2006.01)
  *G01N 35/02* (2006.01)
  *B04B 11/04* (2006.01)
(52) U.S. Cl.
  CPC ......... *G01N 35/0092* (2013.01); *G01N 35/02* (2013.01); *B04B 2011/046* (2013.01); *G01N 2035/0094* (2013.01); *G01N 2035/00495* (2013.01)
(58) Field of Classification Search
  CPC ....... B04B 2011/046; B04B 9/10; B04B 5/00; G01N 35/04; G01N 35/00; G01N 2035/0465; G01N 2035/00495; G01N 2035/0406; G01N 35/02; G01N 35/0092; G01N 2035/0094
  See application file for complete search history.

(56) References Cited

U.S. PATENT DOCUMENTS

| | | | | |
|---|---|---|---|---|
| 5,674,322 | A * | 10/1997 | Kunz | B04B 5/10 127/53 |
| 5,721,676 | A * | 2/1998 | Bolden | A61M 1/387 422/72 |
| 5,740,185 | A * | 4/1998 | Bosse | G11B 20/1833 356/39 |
| 5,814,276 | A * | 9/1998 | Riggs | G01N 35/04 422/549 |
| 5,865,718 | A * | 2/1999 | Chan | B04B 13/00 494/10 |
| 6,461,287 | B1 * | 10/2002 | Glater | B01D 3/08 159/DIG. 11 |
| 7,195,737 | B2 * | 3/2007 | Itoh | B04B 5/0421 422/65 |
| 8,617,041 | B2 * | 12/2013 | Haechler | B04B 13/00 422/72 |
| 8,795,144 | B2 * | 8/2014 | Pedrazzini | B04B 5/0421 494/20 |
| 2004/0022682 | A1 * | 2/2004 | Itoh | G01N 35/04 422/64 |
| 2004/0089737 | A1 * | 5/2004 | Itoh | B04B 5/0421 239/264 |
| 2004/0102920 | A1 * | 5/2004 | Itoh | B04B 5/0414 702/173 |
| 2004/0184958 | A1 * | 9/2004 | Itoh | B04B 5/0421 422/72 |
| 2004/0184959 | A1 * | 9/2004 | Itoh | B04B 5/0421 422/72 |
| 2007/0020764 | A1 * | 1/2007 | Miller | G01N 35/0092 436/45 |
| 2007/0059209 | A1 * | 3/2007 | Pang | G01N 35/0095 422/72 |
| 2009/0047179 | A1 * | 2/2009 | Ping | G01N 35/0095 422/72 |
| 2009/0275458 | A1 * | 11/2009 | Dee | G01N 35/0095 494/10 |
| 2009/0318276 | A1 * | 12/2009 | Miller | B04B 13/00 494/20 |
| 2011/0045958 | A1 * | 2/2011 | Pedrazzini | B04B 5/0421 494/8 |
| 2011/0245061 | A1 * | 10/2011 | Haechler | B04B 13/00 494/8 |
| 2012/0129673 | A1 * | 5/2012 | Fukugaki | G01N 35/00029 494/1 |
| 2013/0307381 | A1 * | 11/2013 | Itoh | G01N 35/04 312/97 |
| 2015/0111299 | A1 * | 4/2015 | Watabe | G01N 35/0095 436/45 |
| 2015/0141232 | A1 * | 5/2015 | Verweij | B04B 5/10 494/16 |
| 2015/0360239 | A1 * | 12/2015 | Yano | B04B 13/00 494/10 |
| 2016/0016183 | A1 * | 1/2016 | Miller | B04B 5/0414 494/1 |
| 2016/0023220 | A1 * | 1/2016 | Miller | B04B 5/0414 494/16 |
| 2017/0021367 | A1 * | 1/2017 | Itoh | B04B 5/0407 |
| 2017/0219616 | A1 * | 8/2017 | Pedrazzini | G01N 35/00009 |
| 2018/0080949 | A1 * | 3/2018 | Jost | G01N 35/0092 |

FOREIGN PATENT DOCUMENTS

| | | | |
|---|---|---|---|
| JP | 11-304806 A | 11/1999 | |
| JP | 2000-084436 A | 3/2000 | |
| JP | 2004230328 A * | 8/2004 | .......... B04B 5/0421 |
| JP | 2004230329 A * | 8/2004 | .......... B04B 5/0421 |
| JP | 2009-515140 A | 4/2009 | |
| JP | 2010-175513 A | 8/2010 | |
| JP | 2011056397 A * | 3/2011 | ............. B04B 5/10 |
| JP | 2011-520109 A | 7/2011 | |
| JP | 2011-525243 A | 9/2011 | |
| JP | 2011189324 A * | 9/2011 | ............. B04B 13/00 |

* cited by examiner

[Fig. 1]
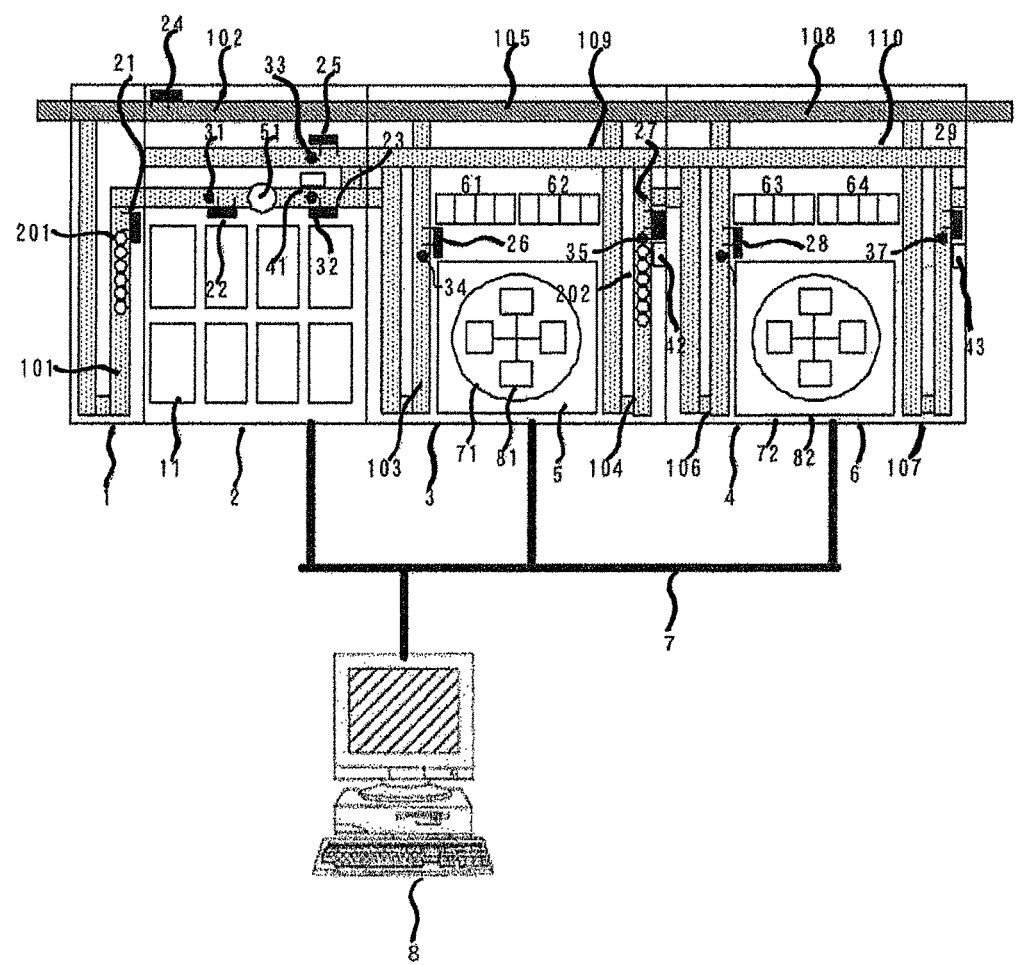

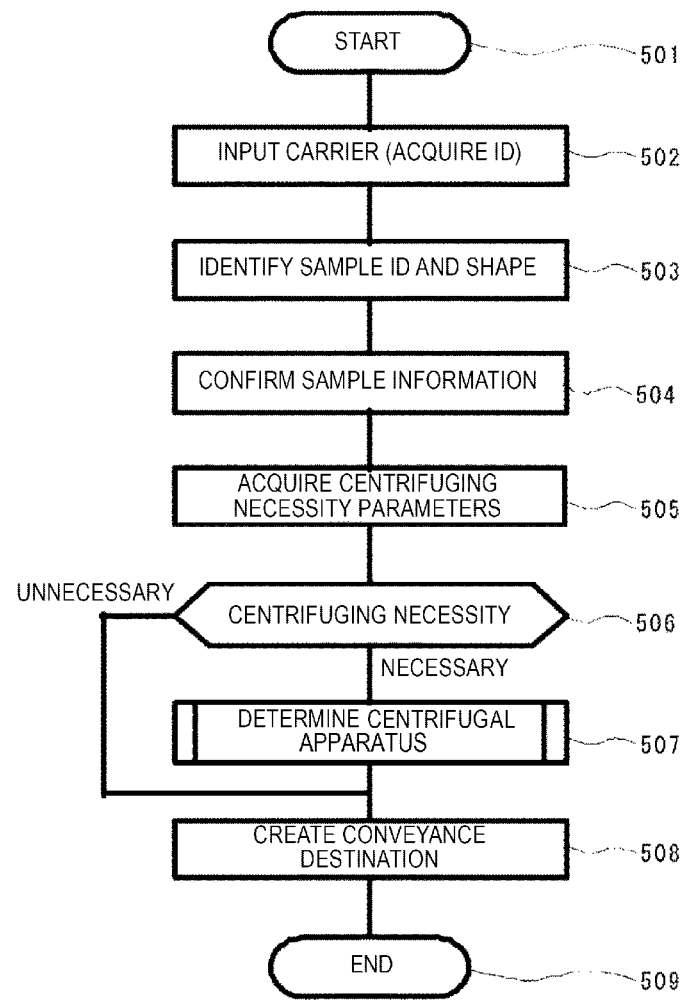
[Fig. 2]

[Fig. 3]
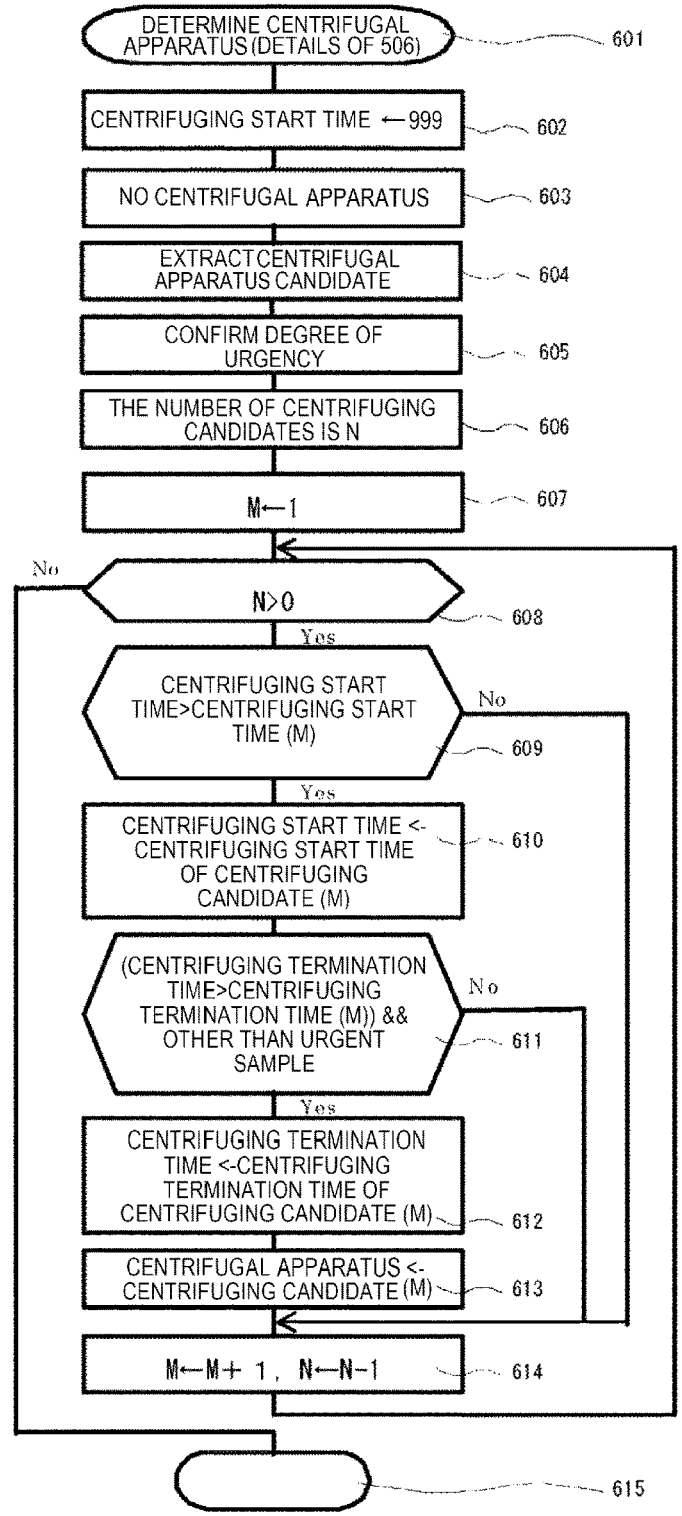

[Fig. 4]

| SAMPLE TYPE | CENTRIFUGING 1 | CENTRIFUGING 2 | CENTRIFUGING 3 |
|---|---|---|---|
| BLOOD SERUM | ☒ | ☒ | ☒ |
| BLOOD PLASMA | ☒ | ☒ | ☒ |
| BLOOD SUGAR | ☒ | ☐ | ☐ |
| COAGULATION | ☐ | ☐ | ☒ |
| URINE | ☐ | ☐ | ☐ |
| . . . | ☐ | ☐ | ☐ |

SAMPLE TYPE CENTRIFUGING CONDITIONS

OK    Cancel

[Fig. 5]

| SAMPLE TYPE CENTRIFUGING CONDITIONS | | | | |
|---|---|---|---|---|
| SAMPLE TYPE | CENTRIFUGING 1 | CENTRIFUGING 2 | CENTRIFUGING 3 | |
| BLOOD SERUM | PRIORITY 1 | PRIORITY 2 | PRIORITY 3 | |
| BLOOD PLASMA | PRIORITY 1 | PRIORITY 2 | PRIORITY 3 | |
| BLOOD SUGAR | PRIORITY 1 | — | — | |
| COAGULATION | — | — | PRIORITY 1 | |
| URINE | — | — | — | |
| . . . | . . . | . . . | . . . | |

OK    Cancel

[Fig. 6]
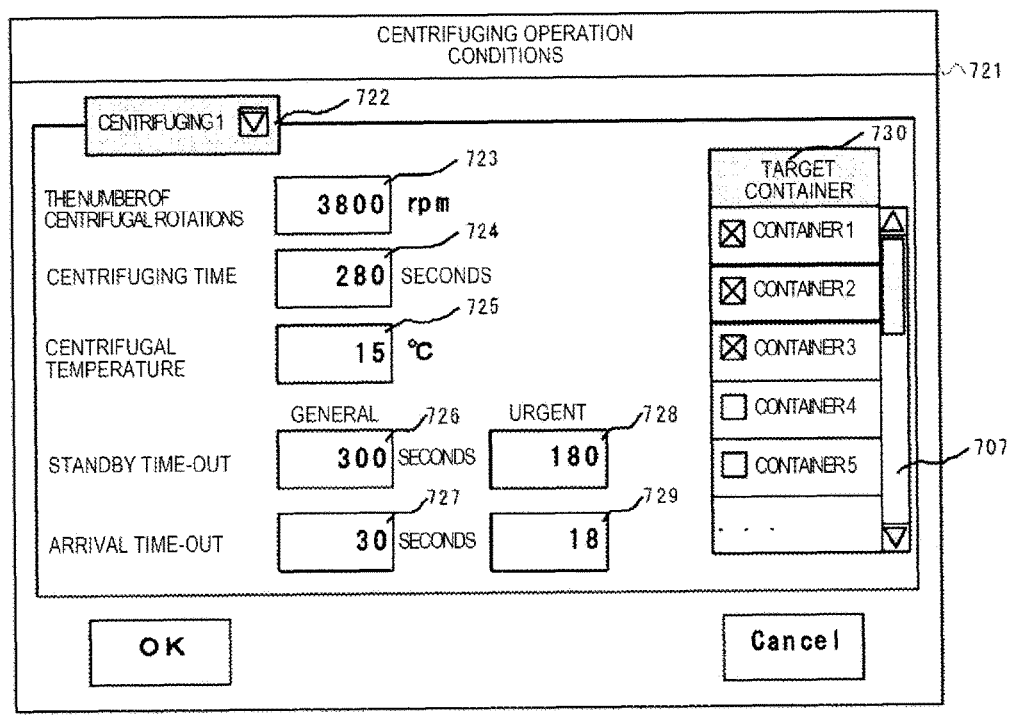

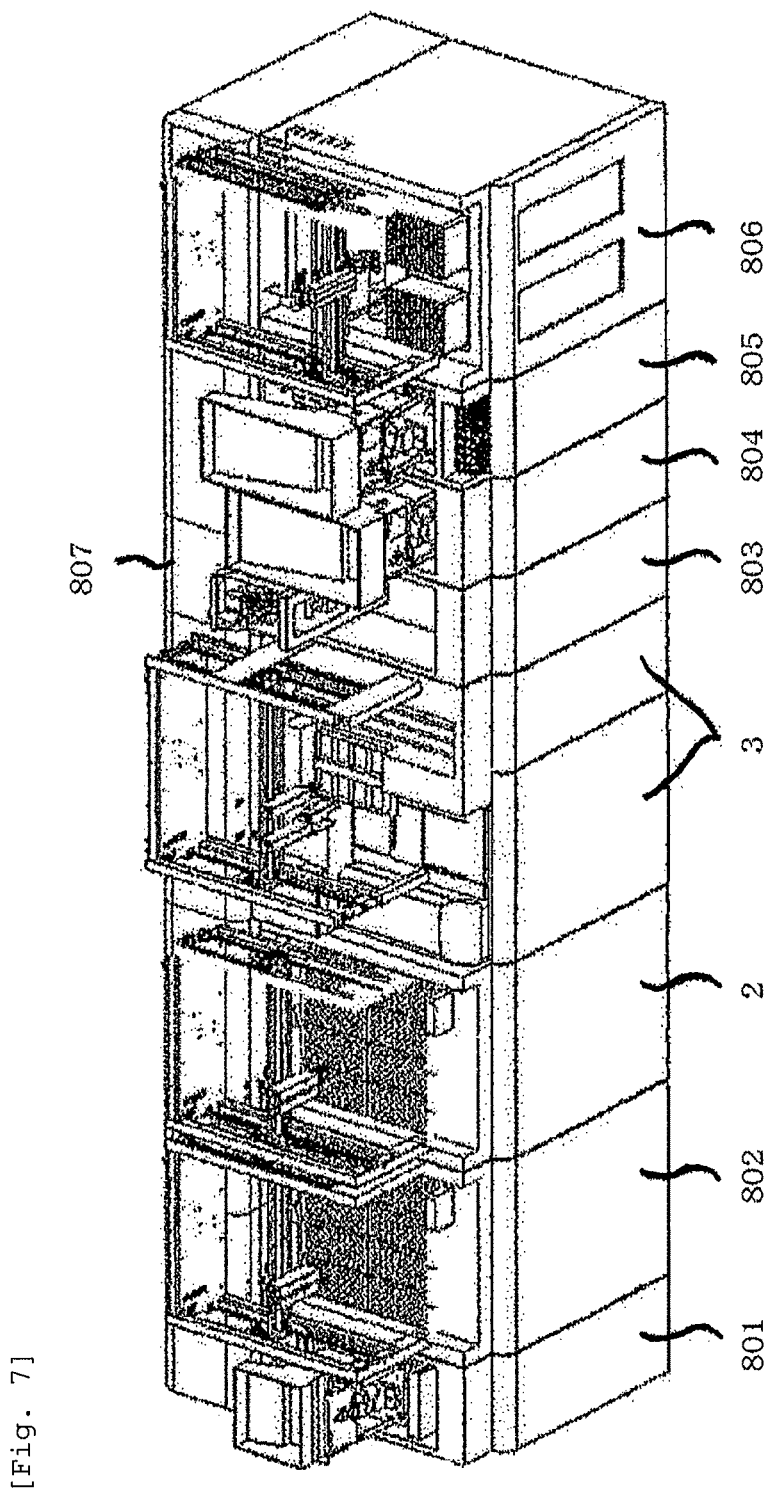
[Fig. 7]

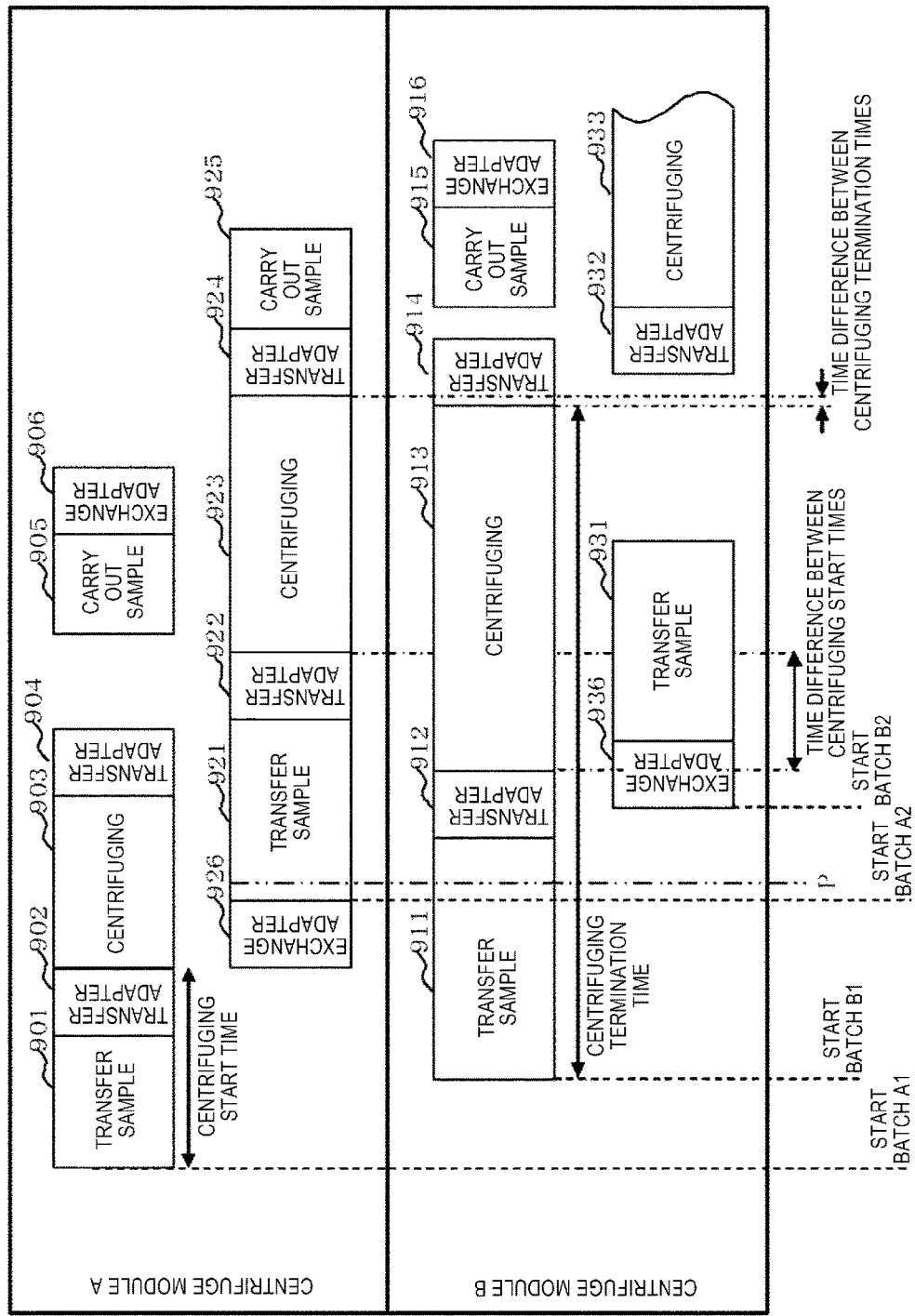
[Fig. 8]

CENTRIFUGING SYSTEM, SAMPLE PREPROCESSING SYSTEM, AND CONTROL METHOD

TECHNICAL FIELD

The present invention relates to a centrifuging system that automatically centrifuges a sample, and a control method thereof.

BACKGROUND ART

In a recent clinical examination field, the labor saving of examination work has been achieved by introducing various types of automation apparatuses and examination systems. In addition, in university hospitals and the like, has become widespread examination before medical care by the reduction in an examination reporting time. In an examination before medical care, a process of collecting samples such as blood and urine from a patient and then reporting an examination result is performed within approximately one hour. Regarding the rapidness of examination reporting, preprocessing work such as centrifuging, the unplugging of a blood collection tube, dispensing for subdividing a sample for each necessary examination, and distribution which are preprocessing steps of sample examination accounts for the majority of an examination time, and thus a reduction in time required for the preprocessing work has become a major problem.

Particularly, a centrifuging process for extracting a serum component from blood collected from a patient includes a process of transferring a sample from a conveyance line to a centrifuge device (process 1), a process of performing centrifuging (process 2), and a process of transferring the sample from the centrifuge device to the sample conveyance line (process 3), and it takes five to fifteen minutes for the whole processing. In addition, the sample preprocessing system and the processes 1 and 3 are real-time processes of sequentially processing samples one by one, while the process 2 of the centrifuge device is a batch process of simultaneously processing several tens of samples. For this reason, when the centrifuge device is incorporated into the sample preprocessing system using a general method, an idle time of the sample preprocessing system is caused, and thus it is not possible to efficiently process a sample. For this reason, in many examination rooms, centrifuging is separately performed by a stand-alone type centrifuge device independent of the sample preprocessing system, which results in a state where the sample preprocessing system cannot sufficiently contribute to labor saving and rapidness of examination work.

In view of the above-described problem, PTL 1 discloses a centrifuge device that improves centrifuging efficiency by combining a plurality of centrifuge devices with a conveyance line portion and pipelining process 1/process 3 and process 2.

CITATION LIST

Patent Literature

PTL 1: JP-A-2000-84436

SUMMARY OF INVENTION

Technical Problem

In the pipelining method disclosed in PTL 1, when times required for the processes 1 to 3 are the same degree, it is possible to exhibit the effect of processing efficiency by including a plurality of centrifuge devices. However, as long as the processes 1 and 3 are real-time processes, it is not possible to guarantee that a constant amount of sample always flows. Thus, it is easily considered that the vacancy of a sample input interval causes the occurrence of a shift in a pipelining timing for the process 2.

In addition, according to this combination of the centrifuge devices and the conveyance line, the plurality of centrifuge devices perform centrifuging under the same conditions, which results in difficulty in simultaneously processing samples having different centrifuging conditions.

Further, when a centrifuge device is added for the purpose of improving centrifuging ability, the conveyance line portion is required to be rearranged, and increases in costs of hardware and software hinder the introduction of centrifuging automation.

Solution to Problem

A configuration of the invention for solving the above-described problem is as follows.

That is, included are an adapter that forms a plurality of batches, sample transfer means for transferring a sample to the adapter, a plurality of centrifuge rotors that perform centrifuging on the adapter in batch units, calculation means for calculating in advance a start timing and a termination timing of the centrifuging in batch units, and control means for controlling the batch transferring the sample on the basis of at least one of the calculated start timing and termination timing.

Advantageous Effects of Invention

A system management unit ascertains states of a plurality of centrifuge devices, and thus it is possible to particularly expect an effect of improving a processing time (turn around time: TAT) by ascertaining centrifuging completion times of the respective centrifuge devices and minimizing a processing time required for centrifuging.

BRIEF DESCRIPTION OF DRAWINGS

FIG. 1 illustrates a portion of a sample preprocessing system according to an embodiment of the invention.

FIG. 2 is a flowchart illustrating determination of a centrifugal apparatus using an input sample (entirety).

FIG. 3 is a flowchart illustrating determination of a centrifugal apparatus using an input sample (details of the determination of the centrifugal apparatus).

FIG. 4 illustrates a screen 1 for registering the setting of sample type centrifuging conditions of the invention.

FIG. 5 illustrates a screen 2 for registering the setting of sample type centrifuging conditions of the invention.

FIG. 6 is a screen for registering the setting of centrifuging operation conditions of the invention.

FIG. 7 is a diagram illustrating the entire sample preprocessing system according to an embodiment of the invention.

FIG. 8 illustrates an example of a time chart of sample conveyance with respect to a plurality of centrifuge modules.

DESCRIPTION OF EMBODIMENTS

Embodiments based on the invention will be described below with reference to the accompanying drawings.

FIG. 7 is an example of a diagram illustrating the entire sample preprocessing system according to the invention.

In FIG. 7, a parent sample is generally input from a sample input module 2 to the sample preprocessing system. The sample conveyed through a conveyance line is taken in a centrifuge module 3, is automatically installed in a centrifuge rotor of a centrifuge device unit to thereby be subjected to centrifuging, and is then conveyed to the conveyance line.

Reference numeral 803 denotes an automatic plug opening module that automatically pulls out a plug attached to a sample container. Reference numeral 804 denotes an automatic barcode attachment module that automatically supplies a container such as a test tube for accommodating a child sample and automatically attaches a barcode label to the test tube. Reference numeral 805 denotes a container and carrier supply module that automatically installs a container in a carrier and carries the container out. Reference numeral 806 denotes a dispensing module that divides child samples distributed from a centrifuged parent sample into containers such as test tubes by a designated amount to thereby generate one or more child samples from the parent sample.

The child samples are samples which are divided to be analyzed in an automatic analysis apparatus, and are carried to the automatic analysis apparatus through a conveyance line connected to the dispensing module 806. The parent sample and the child samples divided for an offline analysis apparatus are conveyed by a return line 807 provided within the sample preprocessing system, are equipped with a plug in an automatic plug closing module 801, and are accommodated in a sample accommodation module 802. A sample conveyed to the automatic analysis apparatus connected to the sample preprocessing system and a sample conveyed to an accommodation unit of the sample preprocessing system are divided by the dispensing module 806, thereby realizing the conveyance of the sample to the automatic analysis apparatus without passing through other modules, in the shortest period of time.

Meanwhile, a configuration diagram of the sample preprocessing system illustrated in FIG. 7 is an example. Since the number of samples to be processed, the scale of a system such as a connection analysis apparatus, and an operation method actually vary according to users, a plurality of sample preprocessing systems may be installed, or a plurality of processing modules may be configured within one sample preprocessing system. In addition, it is possible to add a necessary processing unit or to remove an unnecessary processing unit from the configuration of a sample preprocessing system according to an installation area of an examination room, operation circumstances, and a budget. It is possible to connect a plurality of automatic analysis apparatuses to each other by increasing the number of analysis apparatus connection lines, and thus the sample preprocessing system can be freely and flexibly configured according to a user's circumstances.

First Embodiment

FIG. 1 schematically illustrates a portion of a sample processing system according to an embodiment of the invention. The system includes the centrifuge module 3 and a centrifuge module 4.

The sample input module 2 has a position capable of installing a plurality of sample input trays 11 accommodating a plurality of samples. When samples input by the sample input trays 11 are detected, a sample chuck mechanism not shown in the drawing transfers each of the samples to a holder. In this system, a method of mounting the sample on the holder and conveying the holder having the sample to each processing unit is adopted. A vacant holder for mounting the sample stands by on a vacant holder standby line 101 and is conveyed to a position for placing the sample when detecting the installation of a new tray.

An RFID 31 tag of a conveyed holder 201 is read by an RFID 31, and thus it is possible to individually identify vacant holders 201. Samples input from the sample input module 2 are transferred one by one to the identified holders 201 from the sample input trays 11 by a sample chuck mechanism not shown in the drawing.

Next, the weight of the entire holder having the sample mounted thereon is measured by a test tube weight measurement mechanism 51, and a sample barcode ID attached to the sample and the shape of a container are identified by a barcode reader 41 with a sample container identifying function. Information recognized by the sample input module is notified to a system management unit 8.

The system management unit 8 determines whether or not a centrifuge module can perform centrifuging, on the basis of sample attribute information, sample weight information, sample container shape information which are extracted from the sample barcode ID, and gives an instruction for setting an optimal centrifuge device to be a conveyance destination of the holder on the basis of a determination flow to be described later, and thus the holder is conveyed to an appropriate centrifuge module.

The centrifuge modules 3 and 4 transfer samples to adapters positioned at input centrifuge adapter installation positions 61 and 63 from the conveyed holder. The adapter is provided with a plurality of accommodation units accommodating a sample container. As an example, one adapter can accommodate up to nine sample containers. Under predetermined conditions such as a full adapter or the occurrence of a time-out, the adapter is carried into centrifugal buckets 71 and 72 within respective centrifuge rotors 81 and 82 by an adapter gripper not shown in the drawing, and then centrifuging is performed. In the present embodiment, the centrifuge rotor can centrifuge four adapters at a time, but the number of adapters to be processed is not limited thereto. When the centrifuging is terminated, the adapter gripper transfers the adapters taken out of the centrifugal buckets 71 and 72 to carry-out centrifuge adapter installation positions 62 and 64. Thereafter, samples are transferred one by one to vacant holders from the adapter. Meanwhile, when a larger number of adapters than the number of adapters capable of being centrifuged at a time are set to be handled within one centrifuge module, samples can be transferred to other adapters while some adapters perform centrifugal processing, which leads to a reduction in the idle time of a centrifuge device. Therefore, it is possible to efficiently operate the centrifuge device.

An RFID reader 34 is provided at a sample transfer position of the centrifuge module, and thus the system management unit 8 is notified of an adapter of a centrifuge module on which a conveyed sample is placed. The system management unit 8 creates sample management information on the adapter on the basis of the notified information. Meanwhile, a holder being empty due to the transfer of the sample to the adapter is recovered to a return line 105, is conveyed up to a holder stocker 1, and can be reused for the conveyance of the next sample container.

The centrifuge modules 3 and 4 start centrifuging in accordance with centrifuging operation parameters set in advance. The centrifuging operation parameters include the number of centrifugal rotations 724, a centrifuging time 724, a centrifugal temperature 725, a standby time-out 726, and a conveyance time-out 727, and the like which are set in a centrifuging operation condition setting screen 721 to be described later.

When the centrifuging operation is completed, a sample is taken out from the centrifugal bucket 71 to the carry-out centrifuge adapter installation position 62 for each adapter. In addition, a vacant holder 20 is set to be in a standby state at vacant holder standby lines 104 and 10. Samples mounted on the adapter are transferred one by one to a vacant holder 202 which is standing by at the vacant holder standby line 104. In order to prevent the erroneous handling of a sample, it is confirmed whether or not a sample being processed is correct by reading a sample barcode of a transferred sample by a barcode reader 42 and collating the sample barcode with sample management information on the adapter, and it is preferable to take precautionary measures against the risk of erroneously handling a sample. Thereafter, the system management unit 8 gives an instruction for a destination for a downstream module with reference to sample information and attribute information of the sample, and thus a holder having the sample installed therein is conveyed.

FIG. 2 illustrates a processing flow for the system management unit 8 to determine a conveyance destination of a sample input.

When the sample input module 2 detects the installation of a new sample input tray, the processing of FIG. 2 is started (step 501).

First, in order to acquire IDs for individually identifying carriers (holders), a carrier for mounting a sample is specified, and carrier ID information stored in an RFID tag attached to the carrier is acquired (step 502). Meanwhile, the carrier ID information may be stored in a place other than the RFID tag. For example, a barcode label or a QR code label may be used.

Next, in step 503, sample ID information read from a barcode label attached to a sample container and information such as a type of container is acquired.

These pieces of information are acquired by the sample input module and are transmitted to the system management unit. The system management unit 8 searches for a database on the basis of these pieces of information, and specifies request information and sample attribute information of a process performed on the sample (step 504). When the system management unit 8 does not include information of the sample, it is also possible to receive sample information by inquiry of an examination system (laboratory information system: LIS).

Next, centrifugal necessity setting information is acquired by step 505. Regarding the centrifugal necessity setting information, an operator can determine the necessity of centrifuging on the basis of information that cannot be identified from sample ID information, such as a sample having been subjected to centrifuging by a manual before inputting a sample into a system and a centrifuged sample received from another institution. For example, the sample input module 2 can select the necessity of centrifuging of a sample depending on a position at which the sample is input, and it is possible to determine that samples placed on trays installed at a specific tray installation position of the sample input module 2 do not need to be subjected to centrifuging because they are all centrifuged samples.

In step 506, the necessity of centrifuging of the sample is determined on the basis of the centrifugal necessity setting information of step 505. When the system management unit 8 includes information of the sample and the sample is required to be subjected to centrifuging, a centrifuge module to perform centrifuging is determined on the basis of parameters (described in detail in FIGS. 3 to 5 to be described later) related to centrifuging (step 507).

In order to convey a sample to the determined centrifuge module, conveyance destination information is created (step 508), and then the processing is terminated (step 509). On the other hand, when it is determined in step 506 that the centrifuging of the sample is not necessary, the processing of step 507 is not performed. In the process of creating conveyance destination information in step 508, it is determined that centrifuging is not necessary, a conveyance destination that skips centrifuging is generated.

Details of step 507 in which a centrifugal apparatus performing centrifuging is determined will be described with reference to FIG. 3.

The system management unit 8 acquires information for determining an optimal centrifuge module by the flow of FIG. 2, and performs a process of determining a centrifugal apparatus (step 507, step 601).

First, centrifuge modules capable of performing centrifuging of an identified sample are extracted as centrifuge module candidates. In the extraction of the centrifuge module candidates, the centrifuge module candidates are fixedly set by parameter setting information set by FIGS. 4 to 6 and the next processing.

First, centrifuge modules having centrifuging conditions conforming to each other are extracted on the basis of the request information and the attribute information of the sample which are acquired in step 504 of FIG. 2, centrifuging condition information for each sample type set in advance in FIG. 4 or FIG. 5, and the like (step 604). In addition, it is determined whether or not the sample can be centrifuged by the centrifuge module, on the basis of information regarding the shape of a container which is acquired in container shape identification step 504 and setting information of target container setting 730 of FIG. 6. The extraction of the centrifuge module candidates are performed by integrating these pieces of information.

Meanwhile, when a centrifugal batch having an urgent sample mounted thereon is present in the centrifuge module candidates extracted in step 604, only centrifuge modules including the centrifugal batch are set as centrifugal candidates (step 605). Thereby, the centrifugal batch including the urgent sample is preferentially subjected to centrifuging, and thus it is possible to start centrifuging in a shorter period of time, which leads particularly to an improvement in the processing time (TAT) of the urgent sample.

A total number of centrifuge module candidates extracted is stored as N (step 606). Thereafter, the suitability of an M-th centrifuge module is examined with respect to N centrifuge module candidates. First, M is set to 1, and the examination is sequentially performed from the first centrifuge module (step 607).

A time when the next centrifugal processing is scheduled to start (scheduled centrifugal processing start time: standby time until centrifugal processing is actually performed on a sample taken in a centrifuge unit) is extracted with respect to the M-th centrifuge module, and is compared with a "centrifuging start time" which is initially set (step 609). Meanwhile, when M is set to 1, the "centrifuging start time" is set to 999 as an initial condition (step 602). When the scheduled centrifugal processing start time of the M-th centrifuge module is earlier than the "centrifuging start time" which is already set, the "centrifuging start time" is set to be the scheduled centrifugal processing start time which is scheduled in the M-th centrifuge module.

Next, a time when the next centrifugal processing is scheduled to be terminated (scheduled centrifugal processing termination time: for example, in FIG. 8, a total time of the sum of sample transfer 911, adapter transfer 912, and centrifuging 913) is compared with a "centrifuging termination time" which is initially set with respect to the M-th centrifuge module (step 611). When the scheduled centrifugal processing termination time of the M-th centrifuge module is relatively early, the termination time of the M-th centrifuge module is set as the "centrifuging termination time" (step 612).

When both the "centrifuging start time" and the "centrifuging termination time" are set in the M-th centrifuge module, a "centrifuge module" to be used is set as the "M-th centrifuge module" (step 613).

When either the "centrifuging start time" or the "centrifuging termination time" is later than a time of a centrifuge module other than the M-th centrifuge module, a "centrifuge module" to be used is left intact.

When the above-described processing is terminated, a total number N of centrifuge module candidates to be checked is set to be N−1 and a centrifuge module to be checked next is set to be an M+1 centrifuge module. Then, the processing returns to the processing before step 608 in order to examine the next centrifuge module candidate (step 614).

Next, checking is performed on the M+1-th centrifuge module in the same manner as the above. A scheduled centrifuging start time of an M+1-th centrifuge module candidate is earlier than a scheduled centrifuging start time of an M-th centrifuge module candidate, an M+1-th centrifuging start time is set to be a "centrifuging start time". In contrast, when an M-th centrifuging start time is relatively early, a "centrifuging start time" is set to be the M-th centrifuging start time as it is. Then, the processing proceeds to step 614, and examination is performed on an M+2-th centrifuge module candidate.

When a "centrifuging start time" is reset to be the M+1-th centrifuging start time, comparison between "centrifuging termination times" is performed next. When a scheduled M+1-th centrifugal termination time is earlier than a scheduled M-th centrifugal termination time, a centrifuging termination time of the M+1-th centrifuge module candidate is set to be a "centrifuging termination time". In contrast, when an M-th centrifuging termination time is relatively early, a "centrifuging termination time" is set to be a centrifuging termination time of the M-th centrifuge module candidate as it is. Then, the processing proceeds to step 614, and examination is performed on the next centrifuge module.

When both a "centrifuging start time" and a "centrifuging termination time" are reset by a new centrifuge module candidate, a "centrifuge module" to be used is reset as an "M+1-th centrifuge module". On the other hand, when at least one of the "centrifuging start time" and the "centrifuging termination time" is later than a time which is already set, a "centrifuge module" that is already set is not replaced with the centrifuge module candidate. Then, the processing proceeds to step 614, and examination is performed on the next centrifuge module candidate.

When the checking of all of the M centrifuge module candidates extracted in step 604 has been terminated by repeating the above-described operation, conveyance destination information is created so as to perform centrifuging by a centrifuge module candidate which is set as a "centrifuge module" at that point of time (step 508), and a sample container is conveyed.

It is possible to select a centrifuge module having the earliest scheduled centrifuging start time (step 609, step 610) and the earliest scheduled centrifuging termination time (step 611, step 612) at a timing when a sample is input by performing such processing, and thus it is possible to set a centrifuge module performing centrifuging in the shortest centrifugal processing time. This is because the centrifuging time 724 can be set for each centrifuge module in the centrifuging operation condition setting screen 721 to be described later, which allows the optimization of the whole centrifugal processing to be achieved by extracting the earliest centrifuging start time and the earliest centrifuging termination time.

Meanwhile, in the processing flow of FIG. 3, the variable M is set to 1 so as to perform searching from the first centrifuge module candidate (step 607). Meanwhile, here, it is assumed that a plurality of centrifuge modules are disposed in series and are set as first, second, . . . , and M-th centrifuge modules from the upstream side. This is because the upstream of the configuration arrangement of the centrifuge modules is considered to be a preference module. In some cases, the preferential carrying-out of a sample from a centrifuge module positioned on the downstream side leads to a decrease in the occupancy rate of a conveyance line in a centrifuge module portion and thus contributes to a reduction in congestion of a holder having samples mounted thereon. In this case, it is possible to easily cope with a case where a centrifuge module on the downstream side is preferentially used, by setting M to be N in step 607 and setting M to be M+1 and setting N to be N+1 in step 614 in the processing flow of FIG. 3 when centrifuging operation conditions are the same as each other.

Next, screens for setting centrifuging conditions will be described with reference to FIGS. 4 to 6. Each of the screens is displayed on a display device provided in the system management unit 8.

FIG. 4 illustrates an example of a setting screen when three centrifuge modules are connected to the sample preprocessing system. A sample type registered in the system management unit 8 is displayed in a list format in a sample type 702. The necessity of centrifuging in a first centrifuge module 703, the necessity of centrifuging in a second centrifuge module 704, and the necessity of centrifuging in a third centrifuge module 705 can be set in respective centrifuging necessity fields 706. In the case of FIG. 4, although blood serum and blood plasma can be processed by any centrifuge module, a sample for blood sugar and a sample for coagulation can be processed only by the first centrifuge module 703 and the third centrifuge module 705, respectively. Meanwhile, it is generally preferable that a sample type for which the number of requests for processing is large is set to be capable of being processed by a plurality of centrifuge modules. When the setting is terminated, the setting is stored by pressing an "OK button".

FIG. 5 illustrates an example of a sample type centrifugal priority condition screen 711 when three centrifuge modules are connected to the sample preprocessing system.

A priority setting field 712 is provided, and thus it is possible to designate the processing priority of each centrifuge module for each sample type in addition to determining whether or not centrifuging can be performed. In the case of FIG. 5, the first centrifuge unit is given the highest priority and is used for blood serum and blood plasma, and the lowest priority is set for the third centrifuge unit. Similarly in this setting screen, the setting is stored by pressing an "OK button" after the setting is terminated. A sample type centrifuging condition 701 of FIG. 4 is the necessity of centrifuging. However, in FIG. 5, it is possible to designate the processing priority of each centrifuge module for each sample type by providing the centrifuging priority setting field 712, in addition to the necessity of centrifuging. FIG. 6 illustrates the centrifuging operation condition setting screen 721 for setting centrifuging conditions with respect to each centrifuge module.

In this screen, a centrifuge module for which centrifuging operation conditions are desired to be set is set through a centrifuge unit selection window 722, and thus it is possible to set centrifuging operation conditions of any desired centrifuge module. In the present embodiment, items that can be set in this screen includes the number of centrifugal rotations, a centrifuging time, a centrifugal temperature, a target container, the setting of standby time-out times of a general sample and an urgent sample, and the setting of an arrival time-out time. However, all of the items are not necessarily set, and only some of the items may be able to be set, and other conditions may be able to be set.

Meanwhile, regarding the target container 730 as one of the centrifuging conditions set in this screen, it is preferable that containers capable of being processed in the sample preprocessing system are defined in advance and are registered in identifiable container units. Information of a target container is information serving as an important factor for precisely operating a mechanism that performs processing on a sample container, including the barcode reader 41 with a sample container identifying function.

Further, a standby time-out 726 for a full centrifuge adapter of a general sample and a standby time-out 727 for a full centrifuge adapter of an urgent sample can be individually set, and thus it is possible to reduce a centrifuging start time of the urgent sample. Thereby, a centrifuging termination time of the urgent sample is drastically reduced compared to a centrifuging termination time of a sample other than the urgent sample, and thus it is possible to achieve a reduction in the entire processing time. Accordingly, only the centrifuging start time is used as a criterion with respect to the urgent sample, and thus an optimal centrifuge module may be selected on the basis of only the centrifuging start time.

In this manner, means for setting centrifuging conditions is included for each centrifuge device, and thus it is possible to reduce an idle time of the centrifuge device and to process many types of samples.

FIG. 8 illustrates an example of a time chart regarding centrifugal processing time.

FIG. 8 is a time chart of processing performed by two centrifuge modules of a centrifuge module A and a centrifuge module B which are included in a system. In the centrifuging operation condition setting screen 721, a centrifuging time of the centrifuge module A is set to be shorter than a centrifuging time of the centrifuge module B, and a standby time-out of the centrifuge module A is set to be shorter than a standby time-out of the centrifuge module B. Thereby, the centrifuge module A can centrifuge a greater number of samples. Each centrifuge module has a structure capable of simultaneously processing two batches in parallel. That is, a configuration is adopted in which a process of transferring a sample is performed on an adapter constituting one batch while a sample placed on an adapter constituting the other batch is centrifuged by being rotated at a high speed by a centrifuge unit, thereby reducing an idle time of the centrifuge unit to the maximum.

Meanwhile, in the following embodiment, the batches included in the centrifuge module A are assumed to be a batch A1 and a batch A2, and the batches included in the centrifuge module B are assumed to be a batch B1 and a batch B2. The system management unit 8 calculates scheduled start times and scheduled termination times of a sample carrying-in process, an adapter carrying-in process, a centrifuging process, an adapter carrying-out process, a sample carrying-out process, and an adapter exchange process on the basis of centrifuging conditions set in a centrifuging operation condition setting screen and times required for the processes to thereby create a time chart. At this time, it is necessary to note that usage timings of mechanisms (for example, a sample chuck mechanism, an adapter gripper mechanism, and the like) used in common between a plurality of batches do not overlap each other. According to the created time chart, an execution timing of a sample transfer process 921 of the batch A2 of the centrifuge module A partially overlaps an execution timing of a sample transfer process 911 of the batch B1 of the centrifuge module B, and thus it is necessary to examine into which batch a sample is carried.

When a general sample is input at a point P, the system management unit 8 extracts centrifuge module candidates by the flow of FIG. 3 on the basis of information regarding the acquired sample (step 604), and determines an optimal centrifuge module in performing centrifuging (step 613). In the case of a general sample, a centrifuge module having an earliest "scheduled centrifuging start time" and an earliest "scheduled centrifuging termination time" is selected on the basis of a calculated time chart. In the present embodiment, since the batch B1 of the centrifuge module B has both an earliest centrifuging start time and an earliest centrifuging termination time, centrifuging is performed by the batch B1 of the centrifuge module B.

On the other hand, when an urgent sample is input at the point P, step 612 and step 613 are skipped by the determination of step 611 of FIG. 3, and thus a module to perform centrifuging is determined on the basis of only a "scheduled centrifuging start time". In the present embodiment, a start time of the centrifuging 913 of the batch B1 in the centrifuge module B is earliest, and thus the centrifuge module B serves as a conveyance destination of the urgent sample. Meanwhile, when a time-out time of the urgent sample is set to be shorter than that of the general sample in the centrifuging operation condition setting screen 721, a time-out time for an urgent sample is applied to the centrifuge module B, and thus the sample transfer process 911 in the centrifuge module B is shortened, which results in an inevitable reduction in a centrifuging termination time.

Meanwhile, the sample transfer process 911 to the centrifuge module B is shortened, and thus it is also considered that the adapter 62 used in the batch B1 does not become full. However, even in this case, samples are intensively transferred in the sample transfer process 921 to an adapter constituting the batch A2 of the centrifuge module A, and thus start times of the subsequent adapter transfer process 922 and centrifugal process 923 are advanced. As a result, it is also possible to advance the processing times of the other batches.

In recent years, an examination system has been increased in size by the reorganization of examination rooms. In a sample preprocessing system having a plurality of centrifuge units incorporated thereinto, it is required to cope with problems such as the centrifuging of many types of samples in the same sample preprocessing system and a significant reduction in a sample preprocessing time of an urgent sample. For this reason, it is necessary to centrifuge many types of samples while improving an operation rate of the plurality of centrifuge units and reducing TAT of the sample preprocessing system.

According to the invention, in a system including a plurality of centrifuge devices, it is possible to improve TAT by minimizing a time required for centrifuging. In addition, centrifuging conditions of the centrifuge devices are parameterized, and thus it is possible to select a centrifuge device from the shape of a sample container and the attribute information of a sample which conform to the centrifuging conditions and to input many types of samples without consciousness.

Second Embodiment

A second embodiment of the invention will be described below.

When there are small differences between "centrifuging start times" of batches and between "centrifuging termination times" thereof, it is considered that the preferential conveyance of a sample from a centrifuge module positioned on the downstream side leads to a reduction in the occupancy rate of a conveyance line in a centrifuge module portion and thus contributes to a reduction in congestion of a holder having samples mounted thereon. In this case, in addition to the centrifuging start time determination step 609 and the centrifuging termination time determination step 611 of FIG. 3, a difference between a centrifuging start time (centrifuging termination time) which is already set and a centrifuging start time (centrifuging termination time) compared therewith this time is also examined. Only when the time difference is equal to or greater than a threshold value, are the "centrifuging start time" and the "centrifuging termination time" updated. When the time difference is equal to or less than the threshold value, a centrifuge module positioned on the downstream side is set. Thereby, it is possible to perform processing also taking a load on a conveyance line into consideration. Other matters are the same as those in the other embodiments, and thus a detailed description thereof will be omitted here.

Third Embodiment

Another embodiment of the invention will be described below.

Focusing on a sample input interval of a sample input module, the standby time-out 726 is not likely to occur during predetermined sample transfer processes 901, 911, 921, and 931 in a time period having a large number of samples from morning to afternoon, and thus sample arrival standby is not likely to occur when seen from a centrifuge module.

However, in a time period in which the number of samples is decreased (since afternoon), the standby time-out 726 is expected to frequently occur, and thus it is considered that centrifuging is started in a state where the centrifuge adapters 61 and 63 on the carry-in side do not become full. Further, since only several samples arrive per an hour in operation in the evening and night, an excessive standby time is generated not only in the standby time-out 726 for a general sample of FIG. 6 but also in the sample standby time-out 728 for an urgent sample, and thus it is considered that this leads to an unnecessary delay in reporting an examination result.

Consequently, the usage of batch operation and real-time operation may be mixed with each other by monitoring an arrival interval between the input of a sample required to be subjected to centrifuging from the sample input module 2 and the input of a sample required to be subjected to the next centrifuging. As illustrated in FIG. 6, standby time-outs 726 and 728 and arrival time-outs 727 and 729 are parameterized, and thus it is possible to adjust shares of the batch operation and the real-time operation in accordance with sample arrival states for each delivery destination. Alternatively, as described above, when definitions such as a few types of many samples and many types of few samples can be made depending on time periods, centrifuging operation parameters for each time period are prepared, and a system management unit is provided with a mode switching mode for switching between the centrifuging operation parameters, and thus it is possible to provide a sample preprocessing system having optimal centrifuging efficiency throughout a day. The other matters are the same as those in the other embodiments, and thus a detailed description thereof will be omitted here.

REFERENCE SIGNS LIST

1: holder stocker unit
2: sample input module
3, 4: centrifuge module
5, 6: centrifuge unit
7: communication cable
8: system management unit
11: sample input tray
21, 22, 23, 24, 25, 26, 27, 28, 29: double stopper
31, 32, 33, 34, 35, 36, 37: RFID reader and writer
41: barcode reader with sample container identifying function
42, 43: barcode reader
51: test tube weight measurement mechanism
61, 63: carry-in centrifuge adapter installation position
62, 64: carry-out centrifuge adapter installation position
71, 72: centrifugal bucket
81, 82: centrifuge rotor
101, 104, 107: vacant holder standby line
102, 105, 108: return line
103, 106: centrifugal sample carrying-in line
201, 202, 203: vacant holder
501: step of starting determination flow of centrifugal apparatus of input sample
502: carrier (holder) ID acquisition step
503: sample ID and container shape identification step
504: sample information confirmation step
505: sample container parameter acquisition step
506: centrifuging necessity determination step
507: centrifuge device designation step
508: conveyance destination path creation step
509: step of terminating determination flow of centrifugal apparatus of input sample
601: centrifuge device determination flow start step
602: centrifuging time initialization step
603: designation centrifugal apparatus initialization step
604: step of extracting centrifuge device candidate from sample type
605: centrifugal batch urgent degree confirmation step
606: step of setting the number of centrifuge device candidates
607: processing variable initialization step
608: step of confirming the number of centrifuge device candidates
609: centrifuging start time determination step
610: centrifuging start time setting step
611: centrifuging termination time determination step 612: centrifuging termination time setting step
613: designated centrifugal apparatus setting step
614: change updating step
615: step of terminating determination processing flow of centrifuge device
701: sample type centrifuging condition setting screen (necessity of centrifuging)
702: sample type display field of sample type centrifuging condition setting screen
703: centrifuging necessity column of first centrifuge module of sample type centrifuging condition setting screen
704: centrifuging necessity column of second centrifuge module of sample type centrifuging condition setting screen
705: centrifuging necessity column of third centrifuge module of sample type centrifuging condition setting screen
706: centrifuging necessity field of sample type centrifuging condition setting screen
707: display scroll bar of sample type centrifuging condition setting screen
711: sample type centrifugal priority condition screen
712: centrifugal priority setting field of sample type centrifuging condition setting screen
721: centrifuging operation condition setting screen
722: selection of centrifuge unit in centrifuging operation condition setting screen
723: the number of centrifugal rotations of centrifuging operation condition setting screen
724: centrifuging time of centrifuging operation condition setting screen
725: centrifugal temperature of centrifuging operation condition setting screen
726: general sample standby time-out of centrifuging operation condition setting screen
727: general sample arrival time-out of centrifuging operation condition setting screen
728: urgent sample standby time-out of centrifuging operation condition setting screen
727: urgent sample conveyance time-out of centrifuging operation condition setting screen
730: target container setting of centrifuging operation condition setting screen
801: automatic plug closing module
802: sample accommodation module
803: automatic plug opening module
804: automatic barcode attachment module
805: container and carrier supply module
806: dispensing module
807: return line
901, 911, 921, 931: sample transfer processing time of target sample
902, 912, 922, 932: transfer time of centrifuge adapter to centrifuge rotor
903, 913, 923, 933: centrifuging time
904, 914, 924: transfer time of centrifuge adapter from centrifuge rotor
905, 915, 925: centrifuged sample carry-out time
906, 916, 926, 936: exchange time of centrifuge adapter from carry-out position to carry-in position

The invention claimed is:
1. A centrifuging system comprising:
an input module that inputs a plurality of samples;
a plurality of centrifuge modules including one or more adapter grippers for transferring the input samples to a plurality of adapters forming batches, and a plurality of rotors that centrifuge the samples in batch units;
a conveyance device that conveys the samples from the input module to the centrifuge modules;
a computer connected to the centrifuge modules and programmed to:
ascertain sample attribute information of a given sample from among the input samples and operation states of the plurality of centrifuge modules to thereby extract a plurality of centrifuge module candidates from the plurality of centrifuge modules capable of performing centrifuging of the given sample;
calculate a plurality of respective start timings, for each of the batches included in the centrifuge module candidates, on the basis of at least a standby time-out time or an expected time until the respective batch is fixedly set in a centrifuging operation condition, and calculate a plurality of termination timings on the basis of a sum of the start timings and a plurality of centrifuging times of the centrifuge module candidates; and
select one of the batches and one of the centrifuge modules in which the conveyance device and the sample transfer means transfer the given sample from among the centrifuge module candidates and the batches thereof on the basis of at least one of the calculated start timings and termination timings.

2. The centrifuging system according to claim 1, further comprising: a reading device connected to the computer and configured to identify the sample attribute information from the input samples,
wherein the computer is connected to the reading device, and is further programmed to:
transfer a first one of the input samples to one of the batches for which the start timings is earliest when the sample attribute information indicates the first one of the samples is an urgent sample, and
transfer a second one of the input samples to one of the batches for which the start timings and the termination timings are earliest when the sample attribute information indicates the second one of the input samples is a general sample.

3. The centrifuging system according to claim 2, wherein the computer is further programmed to:
when the sample attribute information indicates a third one of the input samples is an emergency sample, a time-out time of the one of the batches having transferred the urgent sample is reduced.

4. The centrifuging system according to claim 1, further comprising:
a display device connected to the computer,
wherein the computer is further programmed to:
display a screen for setting one or more sample types for each of the centrifuge modules.

5. The centrifuging system according to claim 4, wherein the computer is further programmed to display a screen for setting a priority of the centrifuge modules used for each of the sample types.

6. The centrifuging system according to claim 1, further comprising: a display device connected to the computer,
wherein the computer is further programmed to display a centrifuging operation condition setting screen for setting centrifuging conditions for each of the centrifuge modules.

7. The centrifuging system according to claim 1, wherein the computer is further programmed to:

set a centrifugal processing time for each of the plurality of centrifuge modules based on the centrifuging conditions.

8. A sample preprocessing system comprising:
a processing module that processes a sample; and
a conveyance system that conveys the sample between the centrifuging system according to claim 1 and the processing module.

9. A control method of a centrifuging system including a plurality of rotors that centrifuge a plurality of adapters having a plurality of samples transferred thereto in batch units, the control method comprising:
ascertaining sample attribute information of a given sample from among the input samples and operation states of the plurality of centrifuge modules to thereby extract a plurality of centrifuge module candidates from the plurality of centrifuge modules capable of performing centrifuging of the given sample;
calculating a plurality of respective start timings, for each of the batches included in the centrifuge module candidates, on the basis of at least a standby time-out time or an expected time until the respective batch is fixedly set in a centrifuging operation condition, and calculating a plurality of termination timings on the basis of a sum of the start timings and a plurality of centrifuging times of the centrifuge module candidates;
selecting one of the batches and one of the centrifuge modules from among the centrifuge module candidates and the batches thereof on the basis of at least one of the calculated start timings and termination timings; and
conveying the given sample to the selected batch of the selected centrifuge module.

10. The control method according to claim 9, further comprising:
ascertaining sample attribute information of one of the input samples; and
when the sample attribute information indicates the one of the samples is an urgent sample, the urgent sample is transferred to one of the batches for which the start timing is earliest.

11. The control method according to claim 9, further comprising:
ascertaining sample attribute information of one of the input samples; and
when the sample attribute information indicates the one of the samples is a general sample, the general sample is transferred to one of the batches for which the start time and the termination time are earliest.

12. The centrifuging system according to claim 1, wherein the computer is further programmed to:
set which of the centrifuge modules is capable of performing centrifuging on which of the sample types.

* * * * *